US010660749B2

(12) United States Patent
Figulla et al.

(10) Patent No.: US 10,660,749 B2
(45) Date of Patent: May 26, 2020

(54) HEART VALVE PROSTHESIS FOR PERCUTANEOUS REPLACEMENT OF A TRICUSPID VALVE, AND SYSTEM COMPRISING A HEART VALVE PROSTHESIS OF SAID TYPE

(71) Applicant: NVT AG, Muri (CH)

(72) Inventors: Hans Reiner Figulla, Jena (DE); Alexander Lauten, Kleinmachnow (DE)

(73) Assignee: NVT AG, Muri (CH)

( * ) Notice: Subject to any disclaimer, the term of this patent is extended or adjusted under 35 U.S.C. 154(b) by 190 days.

(21) Appl. No.: 15/407,313

(22) Filed: Jan. 17, 2017

(65) Prior Publication Data

US 2017/0165061 A1 Jun. 15, 2017

Related U.S. Application Data

(63) Continuation of application No. PCT/EP2014/065294, filed on Jul. 16, 2014.

(51) Int. Cl.
*A61F 2/24* (2006.01)
*A61F 2/06* (2013.01)
*A61F 2/856* (2013.01)

(52) U.S. Cl.
CPC .............. *A61F 2/2418* (2013.01); *A61F 2/06* (2013.01); *A61F 2/856* (2013.01); *A61F 2002/061* (2013.01); *A61F 2210/0014* (2013.01)

(58) Field of Classification Search
CPC ........ A61F 2/24; A61F 2/2409; A61F 2/2412; A61F 2/2418; A61F 2/2475; A61F 2/856; A61F 2220/00
See application file for complete search history.

(56) References Cited

U.S. PATENT DOCUMENTS

| 2005/0228496 A1 | 10/2005 | Mensah et al. |
| 2006/0276813 A1 | 12/2006 | Greenberg |
| 2007/0156233 A1 | 7/2007 | Kapadia et al. |
| 2009/0264991 A1 | 10/2009 | Paul, Jr. et al. |
| 2011/0275912 A1 | 11/2011 | Boyden et al. |

(Continued)

FOREIGN PATENT DOCUMENTS

| EP | 2929860 A1 | 10/2015 |
| WO | WO 2006/076890 | 7/2006 |
| WO | WO 2008/070797 | 6/2008 |

OTHER PUBLICATIONS

PCT International Search Report of International PCT Application No. PCT/EP2014/065294 dated Mar. 6, 2015.

(Continued)

*Primary Examiner* — Todd J Scherbel

(74) *Attorney, Agent, or Firm* — Christopher A. Wiklof; James C. Larsen; Launchpad IP, Inc.

(57) ABSTRACT

The invention relates to a heart valve prosthesis for percutaneous replacement of a tricuspid valve including a stent-type support structure and a biological heart valve; the stent-type support structure can autonomously expand from a radially compressed state into a radially expanded state and includes a fluid-tight cover which extends like a tube over at least some portions of the support structure; the heart valve is arranged in a lateral opening in the support structure. Embodiments further relate to a system including a heart valve prosthesis of said type.

18 Claims, 1 Drawing Sheet

(56) References Cited

U.S. PATENT DOCUMENTS

| | | |
|---|---|---|
| 2012/0136430 A1 | 5/2012 | Sochman et al. |
| 2012/0290069 A1* | 11/2012 | Ivancev .................... A61F 2/07 623/1.13 |
| 2013/0150957 A1 | 6/2013 | Weber |
| 2013/0261739 A1 | 10/2013 | Kuehn |
| 2013/0331929 A1 | 12/2013 | Mitra et al. |
| 2014/0114402 A1 | 4/2014 | Ahlberg et al. |
| 2014/0114407 A1 | 4/2014 | Rajamannan |
| 2015/0282958 A1* | 10/2015 | Centola ................. A61F 2/2418 623/2.15 |
| 2018/0147056 A1 | 5/2018 | Lauten et al. |

OTHER PUBLICATIONS

PCT International Search Report and Written Opinion dated Jul. 17, 2015 for International Patent Application No. PCT/EP2015/064745.

* cited by examiner

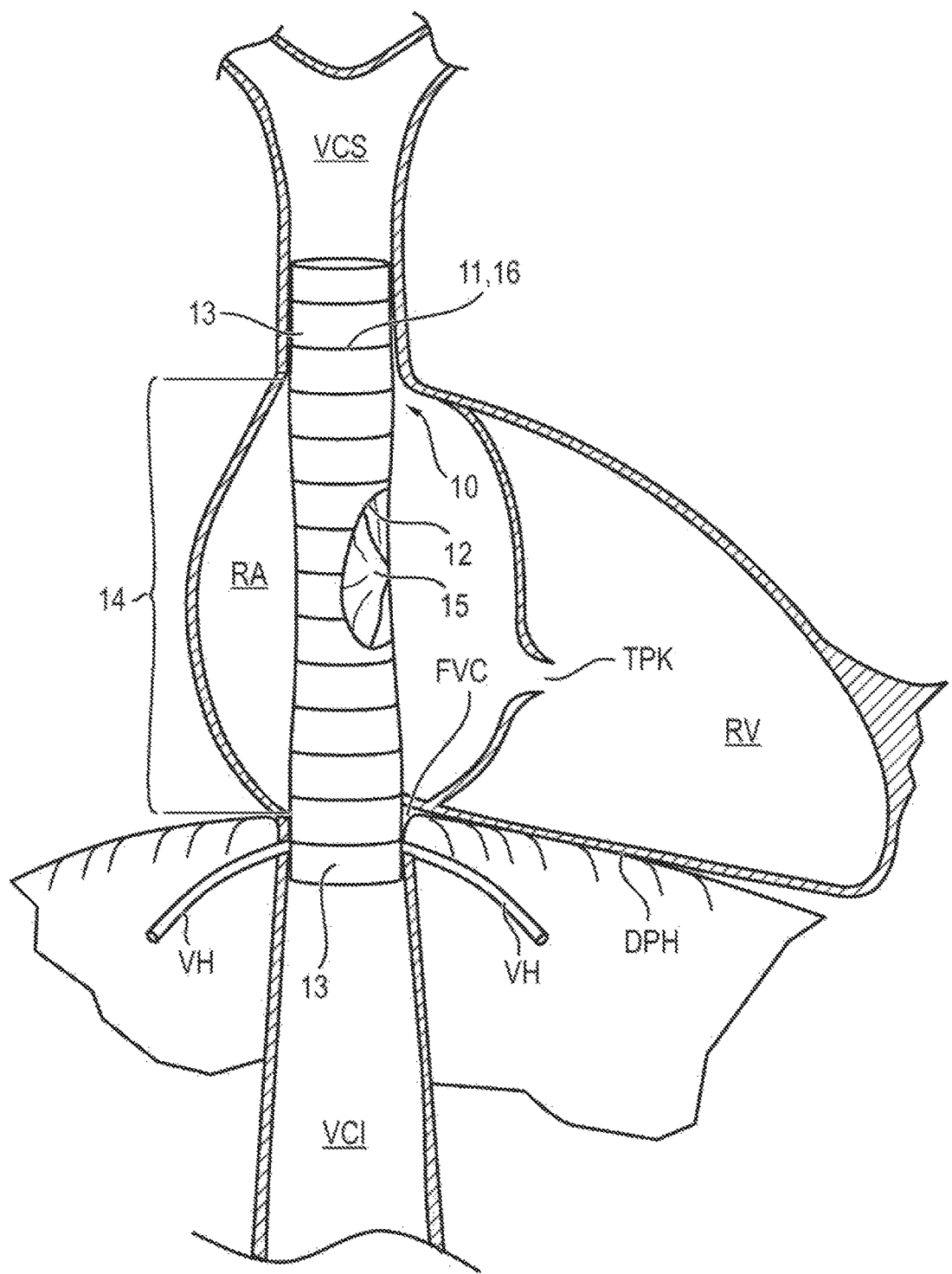

HEART VALVE PROSTHESIS FOR PERCUTANEOUS REPLACEMENT OF A TRICUSPID VALVE, AND SYSTEM COMPRISING A HEART VALVE PROSTHESIS OF SAID TYPE

CROSS-REFERENCE TO RELATED APPLICATIONS

The present application is a U.S. Continuation Application which claims priority benefit under 35 U.S.C. § 120 (pre-AIA) of co-pending International Patent Application No. PCT/EP2014/065294 entitled "HEART VALVE PROSTHESIS FOR PERCUTANEOUS REPLACEMENT OF A TRICUSPID VALVE AND SYSTEM COMPRISING SUCH A HEART VALVE PROSTHESIS," filed Jul. 16, 2014, which, to the extent not inconsistent with the disclosure herein, is incorporated by reference.

SUMMARY

The invention relates to a heart valve prosthesis for the percutaneous replacement of a tricuspid valve. The invention further relates to a system comprising such a heart valve prosthesis.

From the medical perspective, surgically treating tricuspid valve insufficiency poses a great challenge. This condition involves a diminishing ability of the tricuspid valve, which separates the right atrium of the human heart from the right ventricle, to close. Due to the contraction of the right ventricle, this can result in blood being pushed back into the superior and/or inferior vena cava. This ultimately causes volumetric overloading of the right side of the heart as well as increased pressure in the venous circulatory system. In advanced stages, it can result in right heart failure coupled with congestion of the liver and edema formation in peripheral blood vessels.

Depending on the level of severity of the disease, completely replacing the organic tricuspid valve with an artificial heart valve may be necessary. Such surgical procedures are extremely complex and result in considerable stress on the patient. Previous surgical techniques were performed on the open heart such that the patient would need to be hooked up to a heart-lung machine during the operation. This increases the complexity of the surgery and the stress on the patient's circulatory system. Correspondingly, there is a high mortality rate with such operations. There is therefore a need for a minimally invasive alternative for treating tricuspid valve insufficiency.

The invention is based on the task of providing a heart valve prosthesis which is suitable for the percutaneous replacement of a tricuspid valve and which can be surgically implanted in a simple, minimally invasive procedure. The further task of the invention consists of providing a system comprising such a heart valve prosthesis.

With respect to the heart valve prosthesis, the invention solves this task with the subject matter of claim 1 and, with respect to the system, the subject matter of claim 14.

The invention is based on the concept of providing a heart valve prosthesis for the percutaneous replacement of a tricuspid valve comprising a stent-like support structure and a biological heart valve, wherein the stent-like support structure can autonomously expand from a radially compressed into a radially expanded state and has a fluid-tight covering. The fluid-tight covering extends over at least portions of the support structure like a tube. The heart valve is thereby disposed in a lateral opening in the support structure.

The invention is based on the idea of circumventing the complex surgical procedure involved in completely replacing or surgically correcting a tricuspid valve by means of the minimally invasive implanting of a heart valve prosthesis supplemental to the existing tricuspid valve. The heart valve prosthesis, in particular its biological heart valve, thereby at least partly replaces the function of the organic tricuspid valve. The advantage of the heart valve according to the invention consists of it enabling heterotopic, catheter-guided tricuspid valve replacement. In other words, the inventive heart valve prosthesis is suited to minimally invasive surgical implantation. This reduces the stress the patient is subjected to during the operation and lowers the mortality risk.

In particular by virtue of the stent-like support structure, the inventive heart valve prosthesis can be transformed into a radially compressed state and can thus be transluminally guided to the implantation site by a catheter, for example through the femoral vein. Where applicable, this eliminates the need for open-heart surgery.

The heart valve prosthesis autonomously expands at the implantation site after exiting the catheter. Because of the self-expanding properties of the support structure, a radial pressure is exerted on the vascular walls at the site of implantation, this inducing an anchoring of the heart valve prosthesis at the implantation site. At the same time, the heart valve prosthesis seals tight against the organic vascular walls.

The support structure provided with the fluid-tight covering enables the heart valve prosthesis to bridge the right atrium of the human heart and thus join both the superior vena cava as well as the inferior vena cava. In the implanted state, the heart valve prosthesis is preferably anchored on one side in the superior vena cava and on the other side in the inferior vena cava and inasmuch extends right across the right atrium of the heart.

The laterally arranged biological heart valve is preferably oriented toward the tricuspid valve, or the right ventricle of the heart respectively, and thus enables the inflow of venous blood from the caval veins into the right atrium or right ventricle respectively. In this respect, the biological heart valve of the inventive heart valve prosthesis is connected in series to the organic tricuspid valve. The biological heart valve of the heart valve prosthesis thereby takes over the function of the organic tricuspid valve or, respectively, compensates its leakage. The invention inasmuch provides a simple and efficient alternative for the treatment of tricuspid valve insufficiency.

In one preferential embodiment of the inventive heart valve prosthesis, the lateral opening is formed in a common wall plane with the stent-like, in particular tubular, support structure. It can in general be provided for the heart valve prosthesis to be of overall tubular form. The fluid-tight covering of the support structure ensures a conducting function for inflowing blood and prevents blood from flowing uncontrolled into the right atrium. In this respect, the support structure, particularly together with the covering, forms a tubular wall for the heart valve prosthesis.

The lateral opening in the support structure is preferably arranged in a plane with the tubular wall. The lateral opening thus follows the curvature of the tubular wall or, respectively, the course of the common wall plane. Preferably, the lateral opening not only extends through the support structure but also through the covering and inasmuch forms an entryway into the inner lumen of the heart valve prosthesis.

The biological heart valve is disposed within the lateral opening. In other words, the lateral opening is occluded by the biological heart valve. The biological heart valve assumes the function of a valve. In particular, the biological heart valve prevents blood from the right atrium from flowing into the heart valve prosthesis. The biological heart valve can thereby act as check valve only enabling a flow of blood from the caval veins into the right atrium and preventing a return flow.

A further preferential embodiment of the inventive heart valve prosthesis provides for the support structure to comprise two longitudinal-axially end sections adapted to anchoring in the superior and inferior vena cava. The heart valve prosthesis is generally adapted in such a manner that it can connect the superior vena cava and the inferior vena cava together. The length of the heart valve prosthesis is therefore selected such that the longitudinal-axially end sections of the support structure can engage in opening sections of the vena cava forming a transition area to the right atrium. The heart valve prosthesis can inasmuch form a tubular connection between the superior vena cava and the inferior vena cava. The longitudinal-axially end sections are thereby dimensioned, particularly with respect to their sectional diameter, such that they press against the vascular walls of the vena cava with ample radial force and thus anchor the heart valve prosthesis at the implantation site.

It can further be provided for the inventive heart valve prosthesis to have the support structure comprise an atrium section extending between the longitudinal-axially end sections. The atrium section is preferably freely arranged in the right atrium in the implanted state and held in position by the longitudinal-axially end sections. The atrium section therefore mainly has a blood conduit function, whereas the longitudinal-axially end sections mainly have an anchoring function.

In order to fulfill its blood conduit function, the atrium section is preferably of a length which at least corresponds to the distance between the superior vena cava and the inferior vena cava. This ensures that the atrium section provides a fluid connection between the superior vena cava and the inferior vena cava or between the vena cava and the lateral opening in the support structure respectively. It is insofar provided for the lateral opening, in particular the heart valve, to be disposed in the atrium section of the support structure.

It is to be noted in conjunction hereto that the tubular form to the heart valve prosthesis does not necessarily require the heart valve prosthesis to be of uniformly constant sectional diameter. It is instead also conceivable for the sectional diameter to vary along the heart valve prosthesis or the stent-like support structure respectively. For example, the longitudinal-axially end sections can have a larger or smaller sectional diameter than the atrium section between them.

Further noted at this point is that the present application depicts the form of the heart valve prosthesis, in particular the stent-like support structure, in the fully expanded state. There are no external forces acting on the support structure/ heart valve prosthesis in the fully expanded state able to, for example, radially compress the support structure. The fully expanded state therefore essentially corresponds to a dormant state of the heart valve prosthesis. In the implanted state, at least portions of the heart valve prosthesis usually assume a different contour or form, since the radial expansion of the support structure, particularly in the region of the longitudinal-axially end sections, is restricted by coming into contact with body tissues or with the vascular walls respectively.

The support structure can generally be of a wire mesh and/or laser-cut lattice structure respectively enclosing closed meshes or cells. The wire mesh or lattice structure can be provided with a covering, whereby the covering can extend both to an outer circumference as well as to an inner circumference of the lattice structure or wire mesh. It is also possible for a covering to be disposed on both an inner circumference as well as on an outer circumference of the lattice structure/wire mesh.

The use of a wire mesh and/or a laser-cut lattice structure having closed cells has several advantages. On the one hand, such a support structure enables good compression so that a catheter can readily guide the heart valve prosthesis to the site of implantation. At the same time, the diameter ratio between the compressed state and the expanded state is large enough that the support structure can be anchored in the vena cava with a suitable radial force. Moreover, a lattice structure or wire mesh respectively with closed cells or meshes ensures that the support structure can be drawn back into a catheter again, for example in order to remedy incorrect positioning. Lastly, the stability of lattice structures or wire mesh with closed cells or meshes is advantageous for the intended use according to the invention.

The support structure can additionally comprise a passable segment without any covering at least at one longitudinal-axially end. The passable segment can in particular be a ring of meshes or cells arranged adjacently in the circumferential direction of the support structure which, particularly by virtue of not having a covering, are permeable to blood. The passable segment is preferably arranged on a longitudinal-axially end of the support structure. A plurality of hepatic veins lead into the area of the inferior vena cava just prior to entering the right atrium.

In order to still enable the supply of blood from the hepatic veins into the inferior vena cava, the longitudinal-axially end to be positioned in the inferior vena cava can comprise the passable segment. The passable segment is thus preferably arranged so as to be positionable in the region of the inflow of the hepatic veins in the implanted state. Hence, the longitudinal-axially end of the support structure can on the one hand provide ample immobilizing function for the anchoring of the heart valve prosthesis in the inferior vena cava and yet still ensure the inflow of blood from the hepatic veins into the inferior vena cava.

In order to better sustain the inflow of blood from the hepatic veins into the inferior vena cava, it can additionally be provided for the passable segment to have meshes or cells of a larger mesh size than the mesh size of other support structure meshes. This increases the passage area for the blood flowing through and reduces the risk of thromboses forming on the support structure which could lead to an occlusion of the hepatic veins.

It is preferably provided in the present invention for the heart valve to be firmly attached to the support structure within the lateral opening. In particular, the heart valve can be firmly attached to the lattice structure or to the wire mesh of the support structure within the lateral opening. The heart valve can for example be sutured to the support structure. The fixed connection to the support structure, particularly to the supporting mesh or lattice structure, ensures the reliable functioning of the biological heart valve.

The invention further preferentially provides for the covering to be attached in fluid-tight manner to the biological heart valve. It is generally provided for at least the atrium section of the support structure to be completely sealed, whereby the covering effects the seal. Only the lateral opening arranged in the atrium section is without covering, wherein this gap in the covering is filled by the biological heart valve. With the exception of the lateral opening, the covering thus preferably extends over the entire length and the entire circumference of at least the atrium section of the support structure.

The longitudinal-axially end sections of the support structure can be configured without a covering. It is however also possible for the covering to extend over the entire support structure and only be open in the area of the lateral opening. The covering then however attaches in fluid-tight manner to the heart valve fixed in the lateral opening so as to ensure adequate sealing of the biological heart valve. In order to ensure sufficient tightness, the covering can be made from polyester fibers, for example Dacron fibers.

The support structure can comprise a shape-memory material and/or a superelastic material. The support structure can in particular comprise a nickel-titanium alloy, preferably Nitinol. The lattice structure or wire mesh preferably consists of such a nickel-titanium alloy. Such shape-memory materials enable particularly good self-expanding function and exhibit the necessary biocompatibility for implantation in blood vessels. Furthermore, such materials have high enough stability that the stent-like support structure can be of relatively thin configuration. Lastly, nickel-titanium alloys in particular afford good compression of the support structure, which facilitates implantation via catheter.

It is inasmuch preferentially provided for the heart valve prosthesis to generally be able to be implanted transluminally, particularly transfemorally. This ensures a minimally invasive procedure and reduces stress on the patient during the operation. A catheter can thus guide the heart valve prosthesis to the treatment site, whereby the catheter is preferably pushed through the femoral vein and the inferior vena cava to the right atrium.

Alternatively, approach can be made via the vena subclavia. Here, the heart valve prosthesis is pushed to the right atrium through the superior vena cava. In both cases, the heart valve prosthesis is preferably anchored both in the superior as well as the inferior vena cava, whereby the longitudinal-axially end sections of the support structure effect the anchoring. The atrium section is then disposed in the right atrium and inasmuch forms a bridge between the superior vena cava and the inferior vena cava.

In accordance with a supplementary aspect, the invention is based on the concept of providing a system comprising a heart valve prosthesis as described above and a catheter, wherein the heart valve prosthesis can be positioned within the catheter in a compressed state and implanted by the catheter percutaneously, particularly transluminally, preferably transfemorally.

The following will reference the accompanying schematic drawing in describing the invention in greater detail by way of an example embodiment. The single FIGURE thereby shows a side view of an inventive heart valve prosthesis in the implanted state in accordance with a preferential embodiment.

BRIEF DESCRIPTION OF THE DRAWINGS

FIG. 1 shows the area of the right heart comprising a right atrium RA and a right ventricle RV.

DETAILED DESCRIPTION

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1 shows the area of the right heart comprising a right atrium RA and a right ventricle RV. The organic tricuspid valve TPK is arranged between the right atrium RA and the right ventricle RV. The superior vena cava VCS and the inferior vena cava VCI flow into the right atrium RA from opposite sides. The inferior vena cava VCI thereby extends through a diaphragmatic opening FVC located in the diaphragm DPH. A plurality of hepatic veins VH flow into the inferior vena cava VCI in the region of the diaphragmatic opening FVC.

A heart valve prosthesis 10, implanted in the region of the right atrium RA, is provided to at least partly supplant the function of the tricuspid valve TPK caused by its insufficiency. The heart valve prosthesis 10 comprises a support structure 11 having a fluid-tight covering 16. Together with the fluid-tight covering 16, the support structure 11 forms a substantially tube-shaped or tubular implant which extends from the superior vena cava VCS to the inferior vena cava VCI.

The support structure 11 can be divided into three sections, whereby two longitudinal-axially end sections 13 delimit a middle atrium section 14. The longitudinal-axially end sections 13 are arranged in the vena cava VCS, VCI and thereby anchor the heart valve prosthesis 10 at the site of implantation. To that end, it is provided for the support structure 11 or, respectively, the heart valve prosthesis 10 as a whole, to be able to autonomously expand and, upon expanding, exert a radial force which ensures the secure anchoring of the heart valve prosthesis 10 in the vena cava VCS, VCI.

The atrium section 14 of the support structure 11 comprises a lateral opening 12, which is oriented toward the organic tricuspid valve TPK in the depicted embodiment. The lateral opening 12 has a substantially round or oval form and follows the tubular contour of the atrium section 14. A biological heart valve 15 is disposed in the lateral opening 12. The biological heart valve 15 is attached to the covering 16 of the support structure 11 in fluid-tight manner so that blood flowing into the heart valve prosthesis 10 from the vena cava VCS, VCI can only reach the right atrium RA through the biological heart valve 15.

The longitudinal-axially end section 13 of the support structure 11 can additionally comprise a (not shown) passable segment in the region of the inferior vena cava VCI. The passable segment can be without a covering so as to allow blood from the hepatic veins VH to flow into the inferior vena cava VCI.

In general, the accompanying FIGURE thus shows a heart valve prosthesis 10 in accordance with the invention, same in particular being a self-expanding, covered prosthetic conduit supporting a biological heart valve. The covering 16 can be made from a textile structure, for example polyester fibers, particularly Dacron fibers. The heart valve prosthesis 10 can preferably be guided transfemorally to the implantation site by a catheter. The heart valve prosthesis 10 is thereby preferably implanted into the right atrium RA such that the superior and inferior vena cava VCS, VCI are connected to one another by said heart valve prosthesis 10.

The biological heart valve 15, which is disposed in the lateral opening 12, is preferably integrated into the atrium section 14 of the support structure 11 such that the biological heart valve 15 can be positioned at the height of the organic tricuspid valve TPK in the implanted state. The biological heart valve 15 inasmuch takes over the function of the insufficient or leaky organic tricuspid valve TPK. In the implanted state, the inventive heart valve prosthesis 10 enables blood from the superior vena cava VCS and the inferior vena cava VCI to flow into the right atrium RA through the tubular heart valve prosthesis 10 and the laterally positioned biological heart valve.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

The invention claimed is:

1. A heart valve prosthesis, for the percutaneous supplementation or replacement of an organic tricuspid valve, the heart valve prosthesis having an overall tubular form and comprising:
   a stent-type support structure and a biological heart valve,
      the stent-type support structure configured to autonomously expand from a radially compressed state into a radially expanded state; and
   a fluid-tight tubular covering extending over a circumference of at least longitudinally central portions of the stent-type support structure, wherein
      the biological heart valve is disposed in a lateral opening formed in a common tubular wall plane of both the stent-type support structure and the fluid-tight tubular covering, the lateral opening extending through a tubular wall of the stent-type support structure and the fluid-tight tubular covering to form an exit from an inner tubular lumen of the heart valve prosthesis,
      the biological heart valve is disposed within the lateral opening and occluding the lateral opening;
      the heart valve prosthesis is configured to form an overall tubular connection extending between the superior vena cava and the inferior vena cava of an organic heart, and
      when the stent-type support structure is in the radially expanded state, a circumference of the stent-type support structure at one or more of an end of the heart valve prosthesis corresponding to the superior vena cava and an end of the heart valve prosthesis corresponding to the inferior vena cava is at least as large as a transverse circumference of the stent-type support structure and the fluid-tight tubular covering both immediately above the lateral opening and Immediately below the lateral opening.

2. The heart valve prosthesis according to claim 1, characterized in that the lateral opening, arranged in the plane with the tubular wall, follows a curvature of the tubular wall or a course of the common wall plane.

3. The heart valve prosthesis according to claim 1, characterized in that the stent-type support structure comprises two axially longitudinal-axially end sections adapted respectively to anchoring in the superior vena cava and inferior vena cava of the organic heart.

4. The heart valve prosthesis according to claim 3, characterized in that the stent-type support structure comprises an atrium section that extends between the axially longitudinal end sections.

5. The heart valve prosthesis of claim 4, characterized in that the atrium section is of a length that corresponds to a distance between the superior vena cava and the inferior vena cava of the organic heart.

6. The heart valve prosthesis according to claim 4, characterized in that the lateral opening, corresponding to the biological heart valve, is arranged in the atrium section of the stent-type support structure.

7. The heart valve prosthesis according to claim 1, characterized in that the stent-type support structure comprises a wire mesh and/or laser-cut lattice structure respectively enclosing closed meshes or cells.

8. The heart valve prosthesis according to claim 1, characterized in that the stent-type support structure comprises a segment without any tubular covering and permeable to blood, disposed at least at one axially longitudinal-end.

9. The heart valve prosthesis according to claim 8, wherein the stent-type support structure comprises wire mesh and/or laser-cut lattice structure, and characterized in that the segment without any tubular covering and permeable to blood comprises a wire mesh and/or laser-cut lattice structure of a larger mesh size than a mesh size of other wire mesh and/or laser-cut lattice structures of the stent-type support structure.

10. The heart valve prosthesis according to claim 1, characterized in that the biological heart valve is firmly attached to the stent-type support structure within the lateral opening.

11. The heart valve prosthesis according to claim 10, characterized in that the fluid-tight tubular covering is attached in a fluid-tight manner to the biological heart valve fixed in the lateral opening.

12. The heart valve prosthesis according to claim 1, characterized in that the stent-type support structure comprises a shape-memory material and/or a superelastic material.

13. The heart valve prosthesis according to claim 12, characterized in that the shape-memory material and/or the superelastic material comprises a nickel-titanium alloy.

14. The heart valve prosthesis according to claim 13, characterized in that the nickel-titanium alloy comprises Nitinol.

15. The heart valve prosthesis according to claim 1 in combination with a catheter,
   wherein the heart valve prosthesis is configured to be inserted in the radially compressed state by the catheter to position the heart valve prosthesis in the radially compressed state, wherein the heart valve prosthesis is implantable into an organic heart by the catheter percutaneously, and
   wherein there is a diameter ratio between the radially compressed state and the radially expanded state.

16. The heart valve prosthesis according to claim 15, characterized in that the heart valve prosthesis is implantable into the organic heart transluminally.

17. The heart valve prosthesis according to claim 16, characterized in that the heart valve prosthesis is implantable into the organic heart transfemorally.

18. A method of using the heart valve prosthesis of claim 15, comprising implanting the heart valve prosthesis into the organic heart by the catheter.

* * * * *

UNITED STATES PATENT AND TRADEMARK OFFICE
CERTIFICATE OF CORRECTION

| | | |
|---|---|---|
| PATENT NO. | : 10,660,749 B2 | Page 1 of 1 |
| APPLICATION NO. | : 15/407313 | |
| DATED | : May 26, 2020 | |
| INVENTOR(S) | : Hans Reiner Figulla et al. | |

It is certified that error appears in the above-identified patent and that said Letters Patent is hereby corrected as shown below:

In the Claims

- In Claim 1, Column 7, Line 50, "... Immediately below the lateral opening ..." should read -- immediately below the lateral opening --.

- In Claim 3, Column 7, Line 57, "... two axially longitudinally-axially end sections adapted respec- ..." should read -- two axially longitudinal end sections adapted respec- --.

- In Claim 8, Column 8, Line 16, "... blood, disposed at least at one axially longitudinal-end. ..." should read -- blood, disposed at least at one axially longitudinal end. --.

Signed and Sealed this
Seventh Day of July, 2020

Andrei Iancu
*Director of the United States Patent and Trademark Office*